United States Patent
Wolff et al.

(10) Patent No.: US 6,528,511 B2
(45) Date of Patent: Mar. 4, 2003

(54) PARTIAL FATTY ACID OXIDATION INHIBITORS IN THE TREATMENT OF CONGESTIVE HEART FAILURE

(75) Inventors: Andrew A. Wolff, San Francisco; Brent Blackburn, Los Altos, both of CA (US); Hani Naief Sabbah, Waterford, MI (US); William Clark Stanley, Shaker Heights, OH (US)

(73) Assignee: CV Therapeutics, Inc., Palo Alto, CA (US)

( * ) Notice: Subject to any disclaimer, the term of this patent is extended or adjusted under 35 U.S.C. 154(b) by 108 days.

(21) Appl. No.: 09/784,559

(22) Filed: Feb. 15, 2001

(65) Prior Publication Data

US 2001/0047000 A1 Nov. 29, 2001

Related U.S. Application Data

(60) Provisional application No. 60/183,560, filed on Feb. 18, 2000, and provisional application No. 60/219,908, filed on Jul. 21, 2000.

(51) Int. Cl.[7] ............................................ A61K 31/495
(52) U.S. Cl. .................................................. 514/252.12
(58) Field of Search ..................................... 514/252.12

(56) References Cited

U.S. PATENT DOCUMENTS

| | | |
|---|---|---|
| 3,845,770 A | 11/1974 | Theeuwes et al. |
| 4,326,525 A | 4/1982 | Swanson et al. |
| 4,567,264 A | 1/1986 | Kluge et al. |
| 4,902,514 A | 2/1990 | Barclay et al. |
| 4,992,445 A | 2/1991 | Lawter et al. |
| 5,001,139 A | 3/1991 | Lawter et al. |
| 5,023,252 A | 6/1991 | Hseih |
| 5,472,707 A | 12/1995 | Samuels et al. |
| 5,506,229 A | 4/1996 | Dow et al. |
| 5,616,345 A | 4/1997 | Geoghengan et al. |
| 5,906,988 A | 5/1999 | Dow et al. |

FOREIGN PATENT DOCUMENTS

| | | |
|---|---|---|
| WO | WO 99/29305 | 6/1999 |
| WO | WO 00/13687 | 3/2000 |

OTHER PUBLICATIONS

Rousseau, et al., "Novel Metabolic Modulator Ranolazine Selectively Improves Diastolic Function in Heart Failure", *Circulation*, vol. 86, p. 1375 (1992).

Bersin, et al., "Dichloroacetate as Metabolic Therapy for Myocardial Ischemia and Failure", *American Heart Journal*, vol. 134, pp. 841–855 (1997).

Aaker, et al., "Effects of Ranolazine on the Exercise Capacity of Rats with Chronic Heart Failure Induced by Myocardial Infarction", *Journal of Cardiovascular Pharmacology*, vol. 28, pp. 353–362 (1996).

Corder, et al., "Pilot Study Hemodynamic Effects of Ranolazine in the Myocardial Infarcted Rat.", *Fabseb Journal*, vol. 10, p. A428, (1996).

Litwin, et al., Induction of Myocardial Hypertrophy After Coronary Ligation in Rats Decreases Ventricular Dilatation and Improves Systolic Function, *Circulation*, vol. 84, pp. 1819–1827 (1991).

Jones, "Ranolazine Roche Bioscience", *Idrups, Current Drugs, Ltd.*, vol. 2, pp. 1353–1362, (1999).

*Primary Examiner*—Raymond Henley, III
(74) *Attorney, Agent, or Firm*—McDonnell Boehnen Hulbert & Berghoff

(57) ABSTRACT

Methods are disclosed for treating congestive heart failure with partial inhibitors of fatty acid oxidation. The compounds increase cardiac performance without affecting heart rate, blood pressure, or oxygen consumption.

35 Claims, 1 Drawing Sheet

PARTIAL FATTY ACID OXIDATION INHIBITORS IN THE TREATMENT OF CONGESTIVE HEART FAILURE

This application claims priority to U.S. Provisional Application Ser. No. 60/183,560, filed Feb. 18, 2000, and U.S. Provisional Application Ser. No. 60/219,908, filed Jul. 21, 2000 the specifications of each of which are incorporated herein by reference.

BACKGROUND OF THE INVENTION

1. Field of the Invention

This invention relates to a method of treating congestive heart failure by increasing cardiac performance without increasing myocardial oxygen consumption. In particular, the invention relates to a method of treating congestive heart failure with compounds that partially inhibit fatty acid oxidation. This invention also relates to pharmaceutical formulations that maintain plasma concentrations of such compounds at therapeutically effective levels for extended periods of time.

2. Background

Congestive heart failure (CHF) is a major cause of death and disability in industrialized society. It is not a disease in itself, but a condition in which the heart is unable to pump an adequate supply of blood to meet the oxygen requirements of the body's tissues and organs. As a result, fluid accumulates in the heart and other organs, such as the lungs, and spreads into the surrounding tissues. CHF is often a symptom of cardiovascular problems such as coronary artery disease, myocardial infarction, cardiomyopathy, heart valve abnormalities, and the like.

Conventionally, CHF has been treated with a wide variety of drugs, including alpha-adrenergic agonists, beta-adrenergic antagonists, calcium channel antagonists, cardiac glycosides, diuretics, nitrates, phosphodiesterase inhibitors, prazosin, and a variety of vasodilators. All of these drugs, however, have undesirable side-effects. For example, use of alpha-adrenergic agonists results in edema of the peripheral tissues. β-adrenergic agents are effective initially, but prolonged use leads to the progressive development of desensitization to the drug. Treatment with cardiac glycosides is well known to produce toxic side-effects in the CNS, and also the gastrointestinal and respiratory systems. Cardiac glycosides additionally produce pro-arrhythmic effects. Treatment with diuretics may result in a variety of adverse-effects, the most severe of which include electrolyte abnormalities, such as hyponatremia, hypokalemia, and hyperchloremic metabolic alkalosis.

Other problems with current methods of treatment of CHF are exemplified by drugs such as calcium channel antagonists, such as verapamil, diltiazem and nifedipine. These agents initially also produce improvement in the symptoms of CHF, but prolonged use of the agents render them ineffective. Moreover, calcium channel antagonists have been shown to increase the mortality rates in patients thus treated, because such compounds act to increase oxygen consumption, which further stresses the compromised heart.

CHF is characterized by progressive left contractile dysfunction. Accordingly, a desirable approach to treating CHF would be one that enhances contractile function by increasing the efficiency of energy production in the heart thereby increasing cardiac output and mechanical performance.

In the normal heart, most of the energy for contractile function is generated by two processes; 1) oxidative phosphorylation of fatty acids, and, to a lesser extent; 2) oxidation of lactate and glucose, although the latter process is the more efficient. However, in patients with CHF, there is a concomitant increase in fatty acids, so that the amount of energy obtained from the relatively inefficient metabolism of fatty acids increases during exercise-induced stress, and the relative amount of energy generated by the more efficient oxidation of glucose and lactate is reduced. Consequently, the failing heart is further compromised by inefficient energy generation.

Therefore, there is a need for providing a method of treating CHF with agents that switch substrate use in the heart from fatty acids to glucose/lactates, thus improving left ventricle function, without increasing the myocardial oxygen requirement. It is also preferred that the drugs do not act directly to stimulate cardiac contractility, or produce side-effects such as changes in blood pressure and/or heart rate, since they are associated with increased mortality in patients with CHF.

U.S. Pat. No. 4,567,264, the specification of which is incorporated herein by reference, discloses compounds said to have calcium entry blockade properties. In particular, one of those compounds, (±)-N-(2,6-dimethylphenyl)-4-[2-hydroxy-3-(2-methoxyphenoxy)-propyl]-1-piperazineacetamide (known as ranolazine) is undergoing clinical trials for the treatment of angina. Despite the drawbacks generally associated with calcium channel antagonists for the treatment of CHF, it has surprisingly been discovered that the compounds disclosed therein do not have the disadvantages noted above. It has been found that the compounds of '264 exert their beneficial effect as a consequence of having partial fatty acid oxidation (pFox) inhibiting properties, and that they are valuable for the treatment of CHF. In particular, the compounds of the invention switch substrate use in the heart from fatty acids to glucose/lactates, thus improving left ventricle function, while not producing adverse side-effects such as changes in blood pressure and/or heart rate, and do not act directly to stimulate cardiac contractility, all of which would be expected from a calcium entry blocker.

A problem with conventional pharmaceutical formulations of compounds of '264 is that they have low bioavailability, because the high acid solubility of the compounds results in rapid drug absorption and clearance, causing large and undesirable fluctuations in plasma concentration. Also, such compounds have a short duration of action, thus necessitating frequent oral administration for adequate treatment. There is, therefore, a need for a method for administering the compounds of '264, in particular ranolazine, in a dosage form that provides sustained therapeutically effective plasma concentrations of ranolazine for the treatment of congestive heart failure.

U.S. Pat. No. 5,506,229, which is incorporated herein by reference, discloses the use of ranolazine for the treatment of tissues experiencing a physical or chemical insult, including cardioplegia, hypoxic or reperfusion injury to cardiac or skeletal muscle or brain tissue, and for use in transplants.

U.S. Pat. No. 5,472.707, the specification of which is incorporated herein by reference, discloses a high-dose oral formulation employing supercooled liquid ranolazine as a fill solution for a hard gelatin capsule or softgel.

WO0013687, the specification of which is incorporated herein by reference, discloses a sustained release formulation of ranolazine for use in the treatment of angina.

SUMMARY OF THE INVENTION

In a first aspect, the invention provides a method of treating congestive heart failure in mammals, comprising administering to a mammal in need thereof a therapeutically effective amount of a compound that partially inhibits fatty acid oxidation, preferably without effect upon heart rate or blood pressure. Administration is preferably as a bolus or a continuous infusion, or a combination of a bolus and continuous infusion, or as an orally active sustained release formulation.

In a second aspect, this invention provides a method of treating congestive heart failure in mammals, comprising administering to a mammal in need thereof a partial fatty acid oxidation inhibitor of Formula I:

Formula I

[Chemical structure]

wherein:

$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido, provided that when $R^1$ is methyl, $R^4$ is not methyl;

or $R^2$ and $R^3$ together form —OCH$_2$O—;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, or di-lower alkyl amino; or $R^6$ and $R^7$ together form —CH=CH—CH=CH—; or $R^7$ and $R^8$ together form —O—CH$_2$O—;

$R^{11}$ and $R^{12}$ are each independently hydrogen or lower alkyl; and

W is oxygen or sulfur;

and the pharmaceutically acceptable salts and esters thereof.

A preferred compound is named N-(2,6-dimethylphenyl)-4-[2-hydroxy-3-(2-methoxyphenoxy)-propyl]-1-piperazineacetamide, as a racemic mixture, or an isomer thereof.

In a third aspect, this invention provides a method of treating congestive heart failure in mammals, comprising intravenously administering to a mammal in need thereof a therapeutically effective amount of a compound of Formula I, as a bolus or by continuous infusion, or a combination of both.

In a fourth aspect, this invention provides a method of treating congestive heart failure in mammals, comprising administering to a mammal in need thereof a therapeutically effective amount of a compound of Formula I, as a sustained release pharmaceutical composition, preferably orally.

In a fifth aspect, this invention provides a method of treating congestive heart failure in mammals, comprising administering to a mammal in need thereof a compound of Formula I in a manner that maintains plasma concentrations of the compound at therapeutic levels.

In one preferred embodiment, the compound of Formula I is administered by iv infusion in a manner that provides plasma level of the compound of Formula I of at least (0.35±0.03 ng/ml) 350±30 ng/mL for at least 12 hours.

In a second preferred embodiment, the compound of Formula I is administered as a sustained release formulation that maintains plasma concentrations of the compound of Formula I at a maximum of 4000 ng/ml, preferably between about 850 to about 4000 ng base/mL, for at least 12 hours.

DETAILED DESCRIPTION OF THE INVENTION

Definitions and General Parameters

Figure 1:
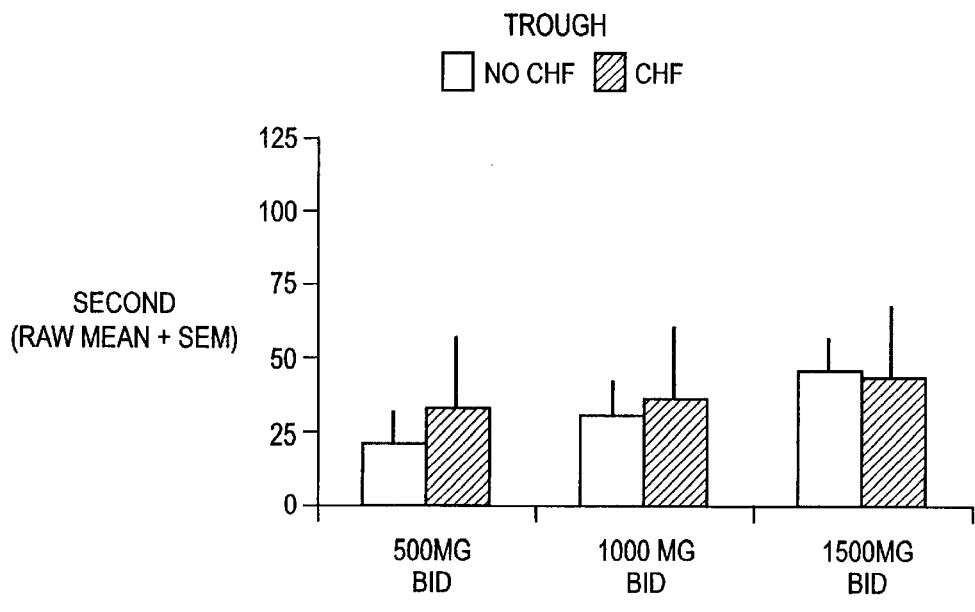
FIG. 1 is a plot of exercise time in patients who were administered a placebo or varying amounts of ranolazine in a sustained release dosage formulation. Data are expressed relative to the control patients treated with placebo.
Figure 1:
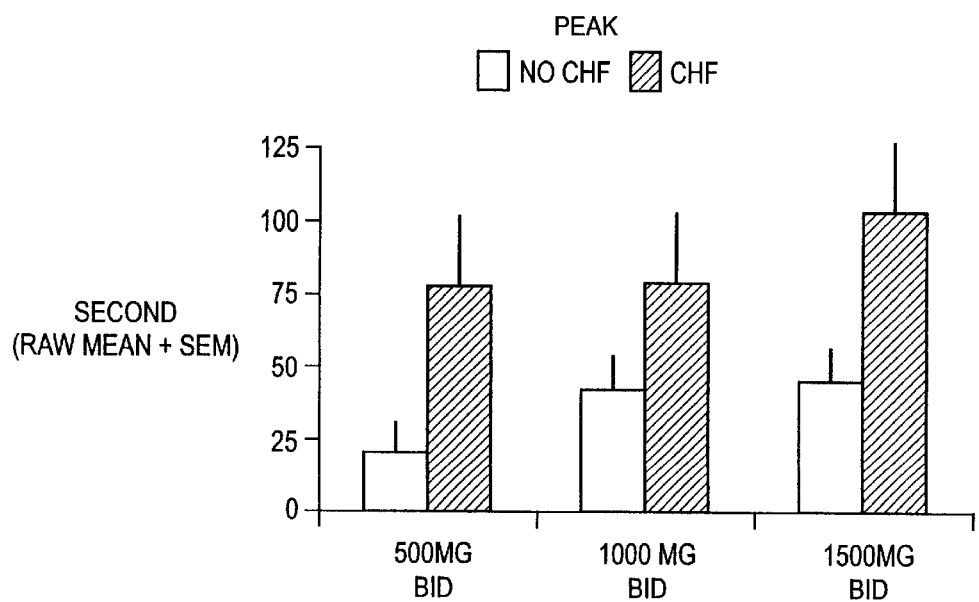

As used in the present specification, the following words and phrases are generally intended to have the meanings as set forth below, except to the extent that the context in which they are used indicates otherwise.

"Aminocarbonylmethyl" refers to a group having the following structure:

[Chemical structure]

where A represents the point of attachment.

"Halo" or "halogen" refers to fluoro, chloro, bromo or iodo.

"Lower acyl" refers to a group having the following structure:

[Chemical structure]

where R is lower alkyl as is defined herein, and A represents the point of attachment, and includes such groups as acetyl, propanoyl, n-butanoyl and the like.

"Lower alkyl" refers to a unbranched saturated hydrocarbon chain of 1–4 carbons, such as methyl, ethyl, n-propyl, and n-butyl.

"Lower alkoxy" refers to a group —OR wherein R is lower alkyl as herein defined.

"Lower alkylthio" refers to a group —SR wherein R is lower alkyl as herein defined.

"Lower alkyl sulfinyl" refers to a group of the formula:

[Chemical structure]

wherein R is lower alkyl as herein defined, and A represents the point of attachment.

"Lower alkyl sulfonyl" refers to a group of the formula:

[Chemical structure]

wherein R is lower alkyl as herein defined, and A represents the point of attachment.

"N-Optionally substituted alkylamido" refers to a group having the following structure:

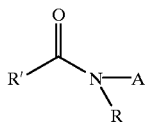

wherein R is independently hydrogen or lower alkyl and R' is lower alkyl as defined herein, and A represents the point of attachment.

"Isomers" refers to compounds having the same atomic mass and atomic number but differing in one or more physical or chemical properties. All isomers of the compound of Formula I are within the scope of the invention.

"Optional" or "optionally" means that the subsequently described event or circumstance may or may not occur, and that the description includes instances where said event or circumstance occurs and instances in which it does not.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl) amines, alkenyl amines, dialkenyl amines, trialkenyl amines, substituted alkenyl amines, di(substituted alkenyl) amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

"Partial fatty acid oxidation inhibitors" refers to compounds that suppress ATP production from the oxidation of fatty acids and consequently stimulate ATP production from the oxidation of glucose and lactate. In the heart, most of the ATP production is acquired through the metabolism of fatty acids. The metabolism of glucose and lactate provides a lesser proportion of ATP. However, the generation of ATP from fatty acids is less efficient with respect to oxygen consumption than the generation of ATP from the oxidation of glucose and lactate. Thus, the use of pFox inhibitors results in more energy production per molecule of oxygen consumed, allowing the heart to be energized more efficiently. PFox inhibitors are especially useful, therefore, in an ischemic environment in which oxygen levels are reduced.

Pharmaceutical Compositions and Administration

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One preferred mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Compounds of Formula I may be impregnated into a stent by diffusion, for example, or coated onto the stent such as in a gel form, for example, using procedures known to one of skill in the art in light of the present disclosure.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The preferred compositions of the invention are formulated so as to provide quick, sustained or delayed release of the active ingredient after administration to the patient, especially sustained release formulations. The most preferred compound of the invention is ranolazine which is named (±)-N-(2,6-dimethylphenyl)-4-[2-hydroxy-3-(2 methoxyphenoxy)propyl]-1-piperazine-acetamide. Unless otherwise stated, the ranolazine plasma concentrations used in the specification and examples refers to ranolazine free base.

Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345, and WO 0013687. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The the intraveous formulation of ranolazine is manufactured via an aseptic fill process as follows. In a suitable vessel, the required amount of Dextrose Monohydrate is dissolved in Water for Injection (WFI) at approximately 78% of the final batch weight. With continuous stirring, the required amount of ranolazine free base is added to the dextrose solution. To facilitate the dissolution of ranolazine, the solution pH is adjusted to a target of 3.88–3.92 with 0.1N or 1N Hydrochloric Acid solution. Additionally, 0.1N HCl or 1.0N NaOH may be utilized to make the final adjustment of solution to the target pH of 3.88–3.92. After ranolazine is dissolved, the batch is adjusted to the final weight with WFI. Upon confirmation that the in-process specifications have been met, the ranolazine bulk solution is sterilized by sterile filtration through two 0.2 μm sterile filters. Subsequently, the sterile ranolazine bulk solution is aseptically filled into sterile glass vials and aseptically stoppered with sterile stoppers. The stoppered vials are then sealed with clean flip-top aluminum seals.

The sustained release formulations of this invention are preferably in the form of a compressed tablet comprising an intimate mixture of compound and a partially neutralized pH-dependent binder that controls the rate of dissolution in aqueous media across the range of pH in the stomach (typically approximately 2) and in the intestine (typically approximately about 5.5).

To provide for a sustained release of compound, one or more pH-dependent binders are chosen to control the dissolution profile of the compound so that the formulation releases the drug slowly and continuously as the formulation passed through the stomach and gastrointestinal tract. The dissolution control capacity of the pH-dependent binder(s) is particularly important in a sustained release formulation because a sustained release formulation that contains sufficient compound for twice daily administration may cause untoward side effects if the compound is released too rapidly ("dose-dumping").

Accordingly, the pH-dependent binders suitable for use in this invention are those which inhibit rapid release of drug from a tablet during its residence in the stomach (where the pH is-below about 4.5), and which promotes the release of a therapeutic amount of compound from the dosage form in the lower gastrointestinal tract (where the pH is generally greater than about 4.5). Many materials known in the pharmaceutical art as "enteric" binders and coating agents have the desired pH dissolution properties. These include phthalic acid derivatives such as the phthalic acid derivatives of vinyl polymers and copolymers, hydroxyalkylcelluloses, alkylcelluloses, cellulose acetates, hydroxyalkylcellulose acetates, cellulose ethers, alkylcellulose acetates, and the partial esters thereof, and polymers and copolymers of lower alkyl acrylic acids and lower alkyl acrylates, and the partial esters thereof Preferred pH-dependent binder materials that can be used in conjunction with the compound to create a sustained release formulation are methacrylic acid copolymers. Methacrylic acid copolymers are copolymers of methacrylic acid with neutral acrylate or methacrylate esters such as ethyl acrylate or methyl methacrylate. A most preferred copolymer is methacrylic acid copolymer, Type C, USP (which is a copolymer of methacrylic acid and ethyl acrylate having between 46.0% and 50.6% methacrylic acid units). Such a copolymer is commercially available, from Röhm Pharma as Eudragit® L 100-55 (as a powder) or L30D-55 (as a 30% dispersion in water). Other pH-dependent binder materials which may be used alone or in combination in a sustained release formulation dosage form include hydroxypropyl cellulose phthalate, hydroxypropyl methylcellulose phthalate, cellulose acetate phthalate, polyvinylacetate phthalate, polyvinylpyrrolidone phthalate, and the like. One or more pH-dependent binders are present in the dosage forms of this invention in an amount ranging from about 1 to about 20 wt %, more preferably from about 5 to about 12 wt % and most preferably about 10 wt %.

One or more pH-independent binders may be in used in sustained release formulations in oral dosage forms. It is to be noted that pH-dependent binders and viscosity enhancing agents such as hydroxypropyl methylcellulose, hydroxypropyl cellulose, methylcellulose, polyvinylpyrrolidone, neutral poly(meth)acrylate esters, and the like, do not themselves provide the required dissolution control provided by the identified pH-dependent binders. The pH-independent binders are present in the formulation of this invention in an amount ranging from about I to about 10 wt %, and preferably in amount ranging from about 1 to about 3 wt % and most preferably about 2.0 wt %.

As shown in Table 1, the preferred compound of the invention, ranolazine, is relatively insoluble in aqueous solutions having a pH above about 6.5, while the solubility begins to increase dramatically below about pH 6.

TABLE 1

| Solution pH | Solubility (mg/mL) | USP Solubility Class |
|---|---|---|
| 4.81 | 161 | Freely Soluble |
| 4.89 | 73.8 | Soluble |
| 4.90 | 76.4 | Soluble |
| 5.04 | 49.4 | Soluble |
| 5.35 | 16.7 | Sparingly Soluble |
| 5.82 | 5.48 | Slightly soluble |
| 6.46 | 1.63 | Slightly soluble |
| 6.73 | 0.83 | Very slightly soluble |
| 7.08 | 0.39 | Very slightly soluble |
| 7.59(unbufferedwater) | 0.24 | Very slightly soluble |
| 7.79 | 0.17 | Very slightly soluble |
| 12.66 | 0.18 | Very slightly soluble |

Increasing the pH-dependent binder content in the formulation decreases the release rate of the sustained release form of the compond from the formulation at pH is below 4.5 typical of the pH found in the stomach. The enteric coating formed by the binder is less soluble and increases the relative release rate above pH 4.5, where the solubility of compound is lower. A proper selection of the pH-dependent binder allows for a quicker release rate of the compound from the formulation above pH 4.5, while greatly affecting the release rate at low pH. Partial neutralization of the binder facilitates the conversion of the binder into a latex like film which forms around the individual granules. Accordingly, the type and the quantity of the pH-dependent binder and amount of the partial neutralization composition are chosen to closely control the rate of dissolution of compound from the formulation.

The dosage forms of this invention should have a quantity of pH-dependent binders sufficient to produce a sustained release formulation from which the release rate of the compound is controlled such that at low pHs (below about 4.5) the rate of dissolution is significantly slowed. In the case of methacrylic acid copolymer, type C, USP (Eudragit® L 100-55), a suitable quantity of pH-dependent binder is between 5% and 15%. The pH dependent binder will typically have from about 1 to about 20% of the binder methacrylic acid carboxyl groups neutralized. However, it is preferred that the degree of neutralization ranges from about 3 to 6%. The sustained release formulation may also contain pharmaceutical excipients intimately admixed with the compound and the pH-dependent binder. Pharmaceutically acceptable excipients may include, for example, pH-independent binders or film-forming agents such as hydroxypropyl methylcellulose, hydroxypropyl cellulose, methylcellulose, polyvinylpyrrolidone, neutral poly(meth) acrylate esters (e.g. the methyl methacrylate/ethyl acrylate copolymers sold under the trademark Eudragit® NE by R öhm Pharma, starch, gelatin, sugars carboxymethylcellulose, and the like. Other useful pharmaceutical excpients include diluents such as lactose, mannitol, dry starch, microcrystalline cellulose and the like; surface active agents such as polyoxyethylene sorbitan esters, sorbitan esters and the like; and coloring agents and flavoring agents. Lubricants (such as talc and magnesium stearate) and other tableting aids are also optionally present.

The sustained release formulations of this invention have a compound content of above about 50% by weight to about 95% or more by weight, more preferably between about 70% to about 90% by weight and most preferably from about 70 to about 80% by weight; a pH-dependent binder content of between 5% and 40%, preferably between 5% and 25%, and more preferably between 5% and 15%; with the remainder of the dosage form comprising pH-independent binders, fillers, and other optional excipients.

One particularly preferred sustained release formulations of this invention is shown below in Table 2.

TABLE 2

| Ingredient | Weight Range (%) | Preferred Range (%) | Most Preferred |
| --- | --- | --- | --- |
| Active ingredient | 0–95 | 70–90 | 75 |
| Microcrystalline cellulose (filler) | 1–35 | 5–15 | 10.6 |
| Methacrylic acid copolymer (Type C) | 1–35 | 5–12.5 | 10.0 |
| Sodium hydroxide | 0.1–1.0 | 0.2–0.6 | 0.4 |
| Hydroxypropyl methylcellulose | 0.5–5.0 | 1–3 | 2.0 |
| Magnesium stearate | 0.5–5.0 | 1–3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl, methylcellulose, cationic methacrylate copolymers (dimethylaminoethyl methacrylate/methylbutyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400–600 mg, 650–850 mg, and 900–1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

It has been found that these methods produce sustained release formulations that provide lower peak plasma levels and yet effective plasma concentrations of compound for up to 12 hours and more after administration, when the compound used as its free base, rather than as the more pharmaceutically common dihydrochloride salt or as another salt or ester. The use of free base affords at least one advantage: The proportion of compound in the tablet can be increased, since the molecular weight of the free base is only 85% that of the dihydrochloride. In this manner, delivery of an effective amount of compound is achieved while limiting the physical size of the dosage unit.

Another advantage of sustained release formulations of this invention is that they are prepared by a process that essentially involves only water as a solvent, and utilizes standard pharmaceutical processing techniques and equipment.

The sustained release formulations of this invention can be used for treating congestive heart failure. It is most preferred that the sustained release dosage formulation be used as a treatment for mammalian congestive heart failure and most preferably as a treatment for congestive heart failure in humans.

The oral sustained release dosage formulations of this invention are administered one, twice; or three times in a 24 hour period in order to maintain a plasma compound level above the threshold therapeutic level and below the maximally tolerated levels, of between about 550 and 7500 ng base/mL in a patient. This corresponds to an amount of compound ranging from about 644 ng/mL to about 8782 ng/mL. Furthermore, the timing of the oral ingestion of the sustained release formulation dosage forms should be controlled to insure that the plasma compound level does not exceed about 7500 ng base/mL and preferably so that the plasma level does not exceed about 5000 ng base/mL an most preferably so that is does not exceed 3800 ng base/mL. In some instances it may be beneficial to limit the peak plasma level to no more than about ng base/mL at the same time, the plasma trough levels should preferably not fall below about 1000 ng base/mL, and in some instances should not fall below 1700 ng base/mL In order to achieve the preferred plasma level of from about 1000 to about 3800 ng base/mL, it is preferred that the oral dosage forms described herein are administered once or twice daily. If the dosage forms are administered twice daily, then it is preferred that the oral dosage forms are administered at about twelve hour intervals.

In addition to formulating and administering oral sustained release dosage forms of this invention in a manner that controls the plasma levels, it is also important to minimize the difference between peak and trough plasma levels. The peak plasma levels are typically achieved at from about 30 minutes to eight hours or more after initially ingesting the dosage form while trough plasma levels are achieve at about the time of ingestion of the next scheduled dosage form. It is preferred that the sustained release dosage forms of this invention are administered in a manner that allows for a peak active ingredient level no more than 8 times greater than the trough level, preferably no more than 4 times greater than the trough and most preferably no greater than 2 times trough level.

The sustained release formulations of this invention provide the therapeutic advantage of minimizing variations in plasma concentration while permitting, at most, twice-daily administration. The formulation may be administered alone, or (at least initially) in combination with an immediate release formulation if rapid achievement of a therapeutically effective plasma concentration is desired or by soluble IV formulations and oral dosage form.

The following Examples are representative of the invention, but are not to be construed as limiting the scope of the claims.

EXAMPLES

Throughout these Examples it should be noted that:
(1) Oral doses of the instant release (IR) formulation were given as capsules or tablets of the dihydrochloride salt and are expressed as the dihydrochloride salt.
(2) Oral doses of the sustained release (SR) formulation were given as tablets of the active ingredient base and are expressed as the free base.
(3) When IR and SR formulations were compared in the same study, doses are expressed in terms of both base and dihydrochloride. The conversion factor for dihydrochloride to base is 0.854 (e.g.: 400 mg dihydrochloride×0.854=342 mg free base equivalent).
(4) All plasma levels and pharmacokinetic parameters are expressed as levels of free base.

Definitons of other terms used in this application are:
ANOVA=analysis of variance
ATP=adenosine triphosphate
$AUC_x$=area under the curve after x hours or time interval
bid=twice daily
$C_{max}$=maximum concentration
$C_{trough}$=residual concentration at 8 hours post-dose for IR formulations and 12 hours post-dose for SR formulations A–C of Example 2.
$C_x$=concentration at time x
ECG=electrocardiographic
ETT=exercise treadmill test
LV=left ventricle
Pbo=placebo
PDH=pyruvate dehydrogenase
tid=three times per day
$T_{max}$=time to maximum concentration It should be noted that the Examples that follow illustrate the preparation and use of representative formulations containing a compound of Formula I, as exemplified by ranolazine.

Example 1

The intravenous formulation of ranolazine is manufactured via an aseptic fill process as follows. In a suitable vessel, the required amount of Dextrose Monohydrate is dissolved in Water for Injection (WFI) at approximately 78% of the final batch weight. With continuous stirring, the required amount of ranolazine free base is added to the dextrose solution. To facilitate the dissolution of ranolazine, the solution pH is adjusted to a target of 3.88–3.92 with 0.1N or 1N Hydrochloric Acid solution. Additionally, 0.1N HCl or 1.0N NaOH may be utilized to make the final adjustment of solution to the target pH of 3.88–3.92. After ranolazine is dissolved, the batch is adjusted to the final weight with WFI. Upon confirmation that the in-process specifications have been met, the ranolazine bulk solution is sterilized by sterile filtration through two 0.2 μm sterile filters. Subsequently, the sterile ranolazine bulk solution is aseptically filled into sterile glass vials and aseptically stoppered with sterile stoppers. The stoppered vials are then sealed with clean flip-top aluminum seals.

Example 2

This Example describes a method of preparing immediate release (IR) ranolazine formulations. Ranolazine dihydrochloride (4000 g), microcrystalline cellulose (650 g), polyvinylpyrrolidone (100 g), and croscarmellose sodium (100 g) powders were intimately mixed together in a Fielder PMA 65 mixer-granulator, and sufficient water was then added, with mixing to form a granulate. The granulate was dried in an Aeromatic Strea-5 fluid bed drier, screened, and mixed with magnesium stearate (100 g). The mixture was filled into hard gelatin capsules to a fill weight of, for example, 500 mg per capsule to achieve a dose of 400 mg of ranolazine dihydrochloride (equivalent to 342 mg of ranolazine free base) per capsule, but may be filled to fill weight of 30 to 400 mg of ranolazine dihydrochloride.

Example 3

This Example describes a method of preparing sustained release (SR) ranolazine formulations. A sustained release (SR) formulation, designated as SR Formulation A, and including pH-dependent and pH-independent binders was prepared by combining Ranolazine (2500 g), methacrylic acid copolymer, Type C (Eudragit® L 100-55—Röhm Pharma) (1000 g), microcrystalline cellulose (Avicel®(100 g) (710 g), and polyvinyl pyrrolidinone powders were intimately mixed together in a Fielder PMA 65 mixer-granulator. The mixture was granulated with a solution of sodium hydroxide (40 g) in water, and a 30% aqueous dispersion of methyl methacrylate/ethyl acrylate copolymer (Eudragit® NE 30 D—Röhm Pharma) (1667 g) was added to the wet mass. The resulting granulate was dried in an Aeromatic Strea-5 fluid bed drier, screened, and then mixed with croscarmellose sodium (100 g) and magnesium stearate (50 g). The mixture was compressed into 684 mg tablets with a Manesty B tablet press to achieve dose of 342 mg of ranolazine free base per tablet. This formulation is referred to as SR Formulation A. SR Formulation B was prepared in the same manner as SR Formulation A except that the Eudragit® L 100-55 was reduced to 500 g, and the Eudragit® NE 30 D was replaced by a 40% aqueous dispersion of a methyl methacrylate/ethyl acrylate copolymer (Eudragit® NE 40 D—Röhm Pharma) (2500 g). The resulting (SR) formulation included 342 mg ranolazine free base per tablet.

In SR Formulation C, ranolazine free base (342 mgs) was blended with microcrystalline cellulose and polyvinyl pyrrolininone K25, granulated with water, dried, and blended with croscarmellose sodium and magnesium stearate. The blend was compressed into tablets and coated with an enteric coating.

SR Formulation D, including only a pH dependent binder was prepared by combining Ranolazine (7500 g), Eudragit® L 100-55 (1000 g), hydroxypropyl methylcellulose (Methocel® E5—source) (200 g), and microcrysalline cellulose (Avicel®) (1060 g) by intimate mixing. The mixed powders were granulated with a solution of sodium hydroxide (40 g) in water (1900 to 2500 grams). The granulate was dried and screened, mixed with magnesium stearate (200 g), and compressed for example into tablets weighing 667 mg to achieve a dose of 500 mg of ranolazine free base per tablet. The tablets were spray coated in a 24 inch Accelacota® cylindrical pan coater with OPADRY film coating solution to a 2–4% weight gain. OPADRY film coating solutions are available in a variety of colors from Colorcon, West Point, Pa. The stepwise procedure for preparing SR Formulation D is as follows:

a) Blend together ranolazine, microcrystalline cellulose, methacrylate copolymer (Type C and hydroxypropyl methyl cellulose using an appropriate blender.
b) Dissolve sodium hydroxide in purified water.
c) Using appropriate granulation equipment, slowly add the sodium hydroxide solution to the blend with constant mixing. Add a further aliquot of water, if necessary.
d) Continue mixing to achieve additional massing. Add a further aliquot of water, if necessary.
e) Dry granulated in a fluid bed dryer.
f) Screen dried granules through an appropriate mill.
g) Add magnesium stearate to the screened granules and blend together. Pass the granulated material through a chilsonator, if needed.
j) Disperse OPADRY powder in water and film-coat using appropriately sized coating
i) Compress the granules into tablets using appropriately sized tooling equipment to a typical level of 2–4% by weight.
Polish with carnauba wax using a typical level of 0.002–0.003% by weight.

Example 4

1. In Vitro Comparison of IR Formulation and SR Formulations

The IR Formulation prepared according to Example 2 and the SR Formulations prepared according to Examples 2A–2C were tested in a USP Apparatus 2 dissolution tester, using 900 mL of 0.1M hydrochloric acid as the dissolution fluid to simulate dissolution in the stomach.

TABLE 3

Percentage of Formulation Dissolved

| Time (hours) | Formulation | | | |
|---|---|---|---|---|
| | IR | A | B | C |
| 0.25 | 88.1 | | | |
| 0.5 | 100.5 | 13.9 | 17.6 | 17.5 |
| 1 | 101.7 | 19.9 | 26.0 | 25.7 |
| 2 | | 27.8 | 47.5 | 35.9 |
| 4 | | 39.0 | 69.2 | 48.4 |
| 8 | | 52.4 | 90.1 | 64.7 |
| 12 | | 61.6 | 99.6 | 74.2 |
| 24 | | 80.8 | 105.6 | 95.4 |

The tabular results (Table 3) show that while the IR Formulation is completely dissolved in no more than 0.5 hours (as expected for an immediate release formulation), SR Formulations A, B, and C displayed a prolonged dissolution of a low pH, as is desirable for a sustained release formulation.

II. In Vivo Comparison of IR Formulation and SR Formulations A, B, and C

Single doses of the IR Formulation prepared according to Example 2 and SR Formulations A and B prepared according to Example 3 were administered to eleven healthy volunteers and their plasma concentrations of ranolazine free base were measured at 0, 20, 40, 60, 90, and 120 minutes, hourly to six hours, twice-hourly to eighteen hours, and at twenty-four hours after administration (SR Formulations only). The results are set forth in Table 4 below.

TABLE 4

| | Formulation | | | |
|---|---|---|---|---|
| | IR | A | B | C |
| $C_{max}$(ISD) (ng/mL) | 1940(807) | 753(264) | 657(316) | 925(747) |
| $C_{trough}$(ISD)(ng/ml | 165(111) | 158(114) | 182(110) | 290(163) |
| $T_{max}$(ISD)(hours) | 1.27(0.5) | 4.09(1.14) | 4.05(1.31) | 6.55(2.93) |
| $AUC_{0-24}$(ISD)(ng.hr/mL) | 6530 | 5640 | 5280 | 5820 |

From Table 4 it is apparent that SR Formulations A, B and C of this invention exhibit dissolution properties which make them suitable for twice daily administration of ranolazine.

Example 5

This Example details a single-ascending dose, crossover-design study that assessed the safety and pharmacokinetic profile of single oral dose of ranolazine base SR Formulation of Example 3D. Human subjects were divided into three groups. Group 1 received 500, 750 and 1000 mg ranolazine SR. Group 2 received 1250 and 1750 mg ranolazine SR. Group 3 received 1500 and 2000 mg ranolazine SR. Each group also had a randomized placebo phase. Mean pharmacokinetic parameters following single oral doses of the ranolazine SR does are detailed in Table 5 below:

TABLE 5

Mean ±SD Pharmacokinetic Parameters (n = 8 except* n = 7)

| Dose SR (mg) | Group | $C_{max}$ (ng/mL) | $C_{trough}$ (ng/mL) | $T_{max}$(hr) | $AUC_{0-30rh}$ (ng.hr/mL) |
|---|---|---|---|---|---|
| 500 | 1 | 883 ± 353 | 382 ± 251 | 4.63 ± 1.19 | 9830 ± 4250 |
| 750 | 1 | 1300 ± 1060 | 455 ± 353 | 4.25 ± 0.886 | 12500 ± 9000 |
| 1000 | 1* | 1610 ± 959 | 695 ± 438 | 5.71 ± 2.14 | 18100 ± 9630 |
| 1250 | 2 | 2210 ± 716 | 943 ± 541 | 6.21 ± 3.52 | 25000 ± 8090 |
| 1500 | 3 | 1980 ± 1050 | 1070 ± 754 | 4.75 ± 0.886 | 25400 ± 16000 |
| 1750 | 2 | 3670 ± 1570 | 2400 ± 1260 | 5.25 ± 2.31 | 49200 ± 18200 |
| 2000 | 3 | 2440 ± 1120 | 1640 ± 937 | 5.21 ± 2.30 | 35400 ± 19100 |

The pharmacokinetic results reported in Table 5 indicate that ranolazine was slowly released from the SR formulation, and consequently the absorption of ranolazine was dissolution-rate limited. This resulted in prolonged plasma drug concentration-time profiles observed at all dose levels, with peak plasma levels at 4 to 6 hours post dose. Over the dose range 500 to 2000 mg, the mean $C_{max}$ and $AUC_{0-30 \, hr}$ increased in an approximately proportional manner, although there appeared to be some deviation from proportionality Group 2.

Example 6

This Example details a double-blind, placebo-controlled, multiple ascending-dose, crossover-designed volunteer study, to evaluate bid dosing. Six subjects received 4 days dosing with ranolazine SR formulation prepared according to Example 2D at 500, 750, and 1000 mg bid, followed by a morning dose on Day 5. Pharmacokinetic results are reported in Table 6, below.

TABLE 6

| Day 5 Ranolazine Pharmacokinetic Parameters (mean ±SD) | | | |
|---|---|---|---|
| Parameter | Ranolazine SR 500 mg bid (n = 7) | Ranolazine SR 750 mg bid (n = 7) | Ranolazine SR 1000 mg bid (n = 7) |
| $C_{max}$ (ng/mL) | 1760 ± 715 | 2710 ± 657 | 3660 ± 1090 |
| $T_{max}$ (hr) | 2.00 ± 1.15 | 4.33 ± 1.62 | 4.17 ± 2.48 |
| $C_{min}$ (ng/mL) | 585 ± 340 | 1260 ± 501 | 1960 ± 812 |

According to Table 6, ranolazine was slowly released from the SR formulation, and consequently the pharmacokinetics were dissolution-rate limited. This resulted in extended plasma drug concentration-time profiles at all dose levels, with peak plasma levels observed at 2 to 4 hours post dose.

These results indicate that useful ranolazine plasma levels can be achieved in humans with dosing of this SR formulation on a bid schedule.

Example 7

This Example evaluated the safety and tolerability of administering racemic ranolazine free base formulations as in Example 3D. The individual and mean concentrations of racemic ranolazine and its enantiomers, (R)-(+)-N-(2,6-dimethylphenyl)-4-[2-hydroxy-3-(2 methoxyphenoxy)-propyl]-1-piperazineacetamide, (S)-(−)-N-(2,6-dimethylphenyl)-4-[2hydroxy-3-(2-methoxyphenoxy)-propyl]-1-piperazineacetamide in human plasma were also determined.

The study was performed with ascending doses of sustained release ranolazine dosage forms. Before and at intervals during and after the dosing period, blood samples were drawn for ranolazine assay and blood pressure, heart rate, ECG and symptoms were monitored throughout. Data summaries were reviewed after each phase before proceeding to the next phase of the study. Eight subjects, all healthy male volunteers aged between 18 and 40 entered and all completed the study and were available for pharmacokinetic and safety analysis. The subjects were each given doses of the various types of ranolazine free base in the form of sustained release tablets including 500 mg and 750 mg tablets or with matching placebo as necessary (2×750 mg size plus 1×500 mg size) to make unit oral doses of 1500 and 2000 mg.

In each phase: one dose bid for four days with a single dose on Day 5. On day 5 each volunteer underwent a full pharmacokinetic profile including supine and erect blood pressure (BP) and heart rate, ECG data, adverse events, clinical chemistry and hematology results, urinalysis results.

Steady state was tested for in each dose level, using $C_{48\ h}$, $C_{72\ h}$ and $C_{96\ h}$ and log transformed data, by analysis of covariance and by testing whether the coefficient for time was significantly different (defined as p<0.05) from 0. These tests were made using two-sided t-tests with estimates of variability from the ANOVA models. Steady state was also assessed by comparing means for $C_{48\ h}$, $C_{72\ h}$ and $C_{96\ h}$ using a mixed effects ANOVA model and untransformed and log, transformed data. For hemodynamic parameters, Day 1 pre-dose treatment means and Day 5 data were compared across treatments via two-sided t-tests using estimates of variability from mixed effects ANOVA models. Ninety and 95% confidence intervals were calculated for the treatment comparisons. No adjustments were made for multiple comparisons.

The mean and standard deviation day 5 pharmacokinetic parameters of ranolazine free base are detailed in Table 7 below and the mean plasma profiles are shown in the figure. Steady-state plasma levels of ranolazine free base appeared to be attained by day 4. Within the dose interval there was a slow rise to maximum levels with $t_{max}$ values ranging from 1 to 6 h post-dose. Thereafter levels declined slowly, producing a small degree of fluctuation in plasma levels over the dosing interval. There appeared to be no differences in the pharmacokinetic parameters of the (+) R and (−) S enantiomers of ranolazine following multiple dosing with this SR formulation.

TABLE 7

| | Day 5 Racemic (RS), (+)R and (−)S Ranolazine SR Pharmacokinetic Parameters | | | |
|---|---|---|---|---|
| | 1500 mg SR bid | | | 2000 mg SR bid |
| Parameter | RS ranolazine | (+)R ranolazine | (−)S ranolazine | RS ranolazine |
| $C_{max}$(ng/ml) | 5284 ± 2434 | 2909 ± 1308 | 2944 ± 1426 | 7281 ± 2700 |
| $C_{min}$(ng/ml) | 2932 ± 1918 | 1436 ± 1046 | 1514 ± 1201 | 4149 ± 2228 |
| Median $t_{max}$ (h) | 4.00 | 4.00 | 4.00 | 4.00 |
| $C_{96h}$(ng/ml) | 3656 ± 1918 | 2009 ± 1137 | 2399 ± 1205 | 5042 ± 1797 |
| $C_{108h}$(ng/ml) | 2942 ± 1937 | 1447 ± 1071 | 1541 ± 1260 | 4398 ± 2396 |
| $AUC_{96-108h}$ (ng.h/ml) | 49516 ± 23945 | 25731 ± 13385 | 26407 ± 14849 | 68459 ± 25842 |
| $C_{ave}$(ng/ml) | 4126 ± 1995 | 2144 ± 1115 | 2201 ± 1237 | 5705 ± 2153 |
| Degree of fluctuation | 0.664 ± 0.336 | 0.833 ± 0.402 | 0.824 ± 0.443 | 0.591 ± 0.240 |

Example 8

This example demonstrates that sustained-release (SR) formulations can keep plasma levels in a therapeutic range with bid dosing, and that such rherapeutic ranges are effective in treating CHF, as evidenced by the improved exercise duration times.

Patients, with or without congestive heart failure were withdrawn from anti-anginal drugs with reproducible anginalimited exercise duration and >1 mm ST depression were randomized to Ran (500 mg bid, 1000 mg bit and 1500 mg bid) and matching placebo (Pbo) in a double-blind, four-period, Latin square crossover design. Exercise treadmill tolerance testing (ETT) was performed following a modified Bruce protocol, at trough (12 hr after dosing) and peak (4 hr after dosing) dosing times. Table 8 shows the results.

TABLE 8

|  | Placebo | | 500 mg bid | | 1000 mg bid | | 1500 mg bid | |
|---|---|---|---|---|---|---|---|---|
|  | trough | peak | trough | peak | trough | peak | trough | peak |
| Exercise Duration (sec) | 511 | 504 | 533 | 532 | 545 | 555 | 559 | 561 |
| p-value vs. placebo | — | — | 0.003 | <0.001 | <0.001 | <0.001 | <0.001 | <0.001 |
| Time to Angina (sec) | 412 | 418 | 437 | 452 | 457 | 474 | 472 | 487 |
| p-value vs. placebo | — | — | 0.005 | <0.001 | <0.001 | <0.001 | <0.001 | <0.001 |
| Time to 1 mm ST Depression (sec) | 448 | 442 | 470 | 479 | 491 | 502 | 514 | 508 |
| p-value vs. placebo | — | — | <0.001 | <0.001 | <0.001 | <0.001 | <0.001 | <0.001 |

Ranolazine improved exercise duration times in comparison to the placebo. Plasma peak and trough concentrations are reported in Table 9 below. Ran had no clinically meaningful effects vs. Pbo on rest or exercise blood pressure or heart rate.

TABLE 9

| Ranolazine Plasma Concentration (Mean (± standard deviation) | | | |
|---|---|---|---|
| Dose | 500 mg BID | 1000 Mg BID | 1500 mg BID |
| Peak (ng/mL) | 1122(727) | 2461(1525) | 3935(2084) |
| Trough (ng/mL) | 846(651) | 1949(1425) | 3266(1973) |

Example 10

The following example shows the results of a dose definition study in which patients were given ranolazine SR in doses of 500 mg bid, 1000 mg bid, 1500 mg bid and placebo. The four treatments were administered in a double-blind fashion and in a random order for treatment periods of one week's duration. At the end of each week of double blind treatment patients underwent exercise testing just prior to dosing ("trough") and 4 hours after dosing, at the expected time of peak plasma levels ("peak").

A plot of exercise time in patients who were administered a placebo or varying amounts of ranolazine in a sustained release dosage formulation. Data are shown in FIG. 1 and are expressed relative to the control patients treated with placebo.

Example 11

The following example is an in vivo model designed to test effect of formulations of ranolazine on congestive heart failure.

The efficacy of ranolazine was studied using a canine model of congestive heart failure. Chronic LV dysfunction and failure was produced by multiple sequential intracoronary embolizations with polystyrene Latex microspheres (70–102 μm in diameter) which results in loss of viable myocardium. In the present study, 13 healthy mongrel dogs weighing between 23 and 25 kg underwent coronary microembolizations to produce heart failure. Intracoronary microembolizations were performed during cardiac catheterization under general anesthesia and sterile conditions. The anesthesia regimen consisted of intravenous oxymorphone hydrochloride (0.22 mg/kg), diazepam (0.17 mg/kg) and sodium pentobarbital (150–250 mg to effect). Dogs underwent an average of 5 microembolization procedures performed 1 to 3 weeks apart. Embolizations were discontinued when LV ejection fraction, determined angiographically, was <30%. Dogs were maintained for a period of 2–3 weeks to ensure that infarctions produced by the last microembolization were completely healed before studies were initiated. An additional group of 8 healthy normal dogs that did not undergo any microembolizations, were also studied so that the hemodynamic effects of ranolazine in the setting of normal physiology could be ascertained. (The study was approved by the Henry Ford Health System Care of Experimental Animals Committee and conformed to the "Position of the American Heart Association on Research Animal Use," adopted by the Association in November 1984, and to the Guiding Principles of the American Physiological Society on use of research animals).

On the day of the study and following general anesthesia, aortic and LV pressure were measured with a catheter-tip micromanometer (Millar Instruments, Houston, Tex.) positioned through a femoral arteriotomy. Single-plane left ventriculograms were obtained during each catheterization after completion of the hemodynamic measurements with the dog placed on its right side. Ventriculograms were recorded on 35 mm cine film at 30 frames per second during the injection of 20 ml of contrast material (Reno-M-60, Squib, Princeton, N.J.). Correction for image magnification was made with a calibrated radiopaque grid placed at the level of the LV. Left ventricular end-systolic and end-diastolic volumes were calculated from ventricular silhouettes using the area-length method. The LV ejection fraction was calculated as the ratio of the difference of end-diastolic volume and end-systolic volume to end-diastolic volume times 100. Stroke volume was calculated as the difference between LV end-systolic and end-diastolic volumes obtained from the ventriculogram. Cardiac output was calculated as the product of stroke volume and heart rate. Extra systolic and post-extra systolic beats were excluded from all analyses.

In each normal or heart failure dog, ranolazine dihydrochloride was administered in saline as an intravenous bolus injection of 0.5 mg/kg followed by a continuous intravenous infusion of 1.0 mg/kg/hr for 40 min. Arterial blood samples were drawn for determination of plasma ranolazine concentration. Samples were obtained at 5, 10, 20, 30, 35 and 40 min after initiation of treatment. Ranolazine was measured by high performance liquid chromatography (HPLC) using mass spectral detection. Following the withdrawal of the final blood sample at 40 min, hemodynamic and angiographic measurements were repeated.

Each animal served as its own control. Pre-treatment values were compared to post-treatment values using a two-tailed paired Student's t-test with significance set at p<0.05. Data are presented as the mean±standard error of the mean.

Results

Arterial ranolazine levels stablized by 10 minutes following the bolus injection (Table 10). The average ranolazine concentration during the final 10 minutes of treatment was 0.30±0.02 ng/mL in normal dogs and 0.33±0.04 ng/mL in dogs with heart failure.

Intravenous administration of ranolazine had no significant effects on heart rate or mean aortic pressure. Ranolazine improved LV systolic function as evidenced by a significant increase in LV ejection fraction, LV peak+dP/dt and LV stroke volume. Ranolazine also improved diastolic function, as evidenced by an increase in LV peak–dP/dt (data not shown).

What is claimed is:

1. A method for treating congestive heart failure in a mammal, which method comprises administering to a mammal in need of such treatment a therapeutically effective amount of a compound that partially inhibits fatty acid oxidation.

2. The method of claim 1, wherein said compound is administered at a dose sufficient to provide a plasma level that inhibits partial fatty acid oxidation without having an effect on heart rate or blood pressure.

3. The method of claim 2, wherein administration of said compound is by a bolus, a continuous infusion, or a combination of bolus and continuous infusion.

4. The method of claim 3, wherein the compound is administered as a solution in dextrose monohydrate at a pH between 3.88 and 3.92.

5. The method of claim 4, wherein the composition is delivered as a bolus injection of 0.5 mg/ml.

6. The method of claim 4, wherein the composition is delivered by continuous infusion of 1.0 mg/kg/hr for 40 minutes.

7. The method of claim 3, wherein the compound is administered by both a bolus and continuous infusion.

8. The method of claim 7, wherein the bolus injection is a dosage of 0.5 mg/ml and the intravenous injection is 1.0 mg/kg/hr for 40 minutes.

9. The method of claim 8, wherein the plasma levels are maintained at 350±30 ng/ml.

10. The method of claim 2, wherein said compound is administered as an orally active sustained release formulation.

11. The method of claim 10, wherein the sustained release formulation is a composition comprising;

| Component | Composition |
| --- | --- |
| Ranolazine | 75.0% |
| Microcrystalline Cellulose | 10.6% |
| Methacrylate Copolymer (Type C) | 10.0% |
| Sodium Hydroxide | 0.4% |
| Hydroxypropyl Methyl Cellulose | 2.0% |
| Magnesium Stearate | 2.0%. |

12. The method of claim 11, wherein the sustained release formulation is administered orally in tablet form once, twice or three times over a 12 hour period.

13. The method of claim 11, wherein the effective plasma level attained by the sustained release formulation is sustained for at least 12 hours.

14. The method of claim 11, wherein the effective plasma level attained by the sustained release formulation is between about 850 to 5000 ug/ml.

15. The method of claim 11, wherein the effective plasma level attained by the sustained release formulation is between about 1000 to 4000 ug/ml.

16. The method of claim 1, wherein the mammal is a human.

17. The method of claim 1, wherein the inhibitor of partial fatty acid oxidation is a compound of Formula I:

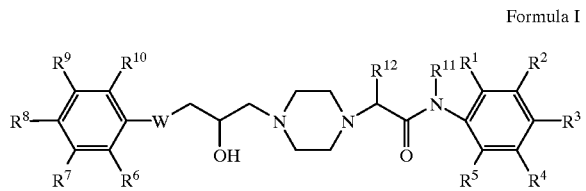

Formula I wherein:
$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido, or $R^2$ and $R^3$ together form —OCH$_2$O—;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, or di-lower alkyl amino; or $R^6$ and $R^7$ together form —CH=CH—CH=CH—; or $R^7$ and $R^8$ together form —O—CH$_2$O—;

$R^{11}$ and $R^{12}$ are each independently hydrogen or lower alkyl; and

W is oxygen or sulfur;

or a pharmaceutically acceptable salt or ester thereof.

18. The method of claim 17, wherein $R^1$, $R^2$, $R^3$, $R^4$, and $R^5$ are hydrogen or lower alkyl, $R^6$, $R^7$, $R^8$, $R^9$, and $R^{10}$ are hydrogen, lower alkyl, or lower alkoxy, and $R^{11}$ and $R^{12}$ are hydrogen.

19. The method of claim 18, wherein $R^2$, $R^3$, $R^4$, $R^7$, $R^8$, $R^9$, and $R^{10}$ are hydrogen, $R^1$, and $R^5$ are lower alkyl, and $R^6$ is lower alkoxy.

20. The method of claim 19, wherein $R^1$ and $R^5$ are both methyl, and $R^6$ is methoxy, namely (±)-N-(2,6-dimethylphenyl)-4-[2-hydroxy-3-(2-methoxyphenoxy)-propyl]-1-piperazineacetamide.

21. The method of claim 20, wherein said compound is administered at a dose sufficient to provide a plasma level that inhibits partial fatty acid oxidation without having an effect on heart rate or blood pressure.

22. The method of claim 21, wherein administration of said compound is by a bolus or a continuous infusion, or a combination of a bolus and continuous infusion.

23. The method of claim 22, wherein the compound is administered as a solution in dextrose monohydrate at a pH between 3.88 and 3.92.

24. The method of claim 22, wherein the composition is administered as a bolus injection of 0.5 mg/ml.

25. The method of claim 22, wherein the composition is administered by continuous infusion of 1.0 mg/kg/hr for 40 minutes.

26. The method of claim 22, wherein the compound is administered by both a bolus and continuous infusion.

27. The method of claim 26, wherein the bolus injection is a dosage of 0.5 mg/ml and the intravenous injection is 1.0 mg/kg/hr for 40 minutes.

28. The method of claim 22, wherein the plasma levels are maintained at 350±30 ng/ml.

29. The method of claim 20, wherein said compound is administered as an orally active sustained release formulation.

30. The method of claim 29, wherein the sustained release formulation is a composition comprising;

| Component | Composition |
|---|---|
| Ranolazine | 75.0% |
| Microcrystalline Cellulose | 10.6% |
| Methacrylate Copolymer (Type C) | 10.0% |
| Sodium Hydroxide | 0.4% |
| Hydroxypropyl Methyl Cellulose | 2.0% |
| Magnesium Stearate | 2.0%. |

31. The method of claim 30, wherein the sustained release formulation is administered orally in tablet form once, twice or three times over a 12 hour period.

32. The method of claim 30, wherein the effective plasma level attained by the sustained release formulation is sustained for at least 12 hours.

33. The method of claim 30, wherein the effective plasma level attained by the sustained release formulation is between about 850 to 5000 ug/ml.

34. The method of claim 33, wherein the effective plasma level attained by the sustained release formulation is between about 1000 to 4000 ug/ml.

35. The method of claim 20, wherein the mammal is a human.

* * * * *